US008066003B2

(12) United States Patent
Cong et al.

(10) Patent No.: US 8,066,003 B2
(45) Date of Patent: Nov. 29, 2011

(54) METHOD FOR IMPROVING CONTROL AND DETECTION PRECISION OF TIDAL VOLUME BY A CALCULATION INTRODUCED WITH R VALUE

(75) Inventors: Yumeng Cong, Beijing (CN); Fei Chang, Beijing (CN); Wei Wang, Beijing (CN)

(73) Assignee: Beijing Aeonmed Co., Ltd., Beijing (CN)

( * ) Notice: Subject to any disclaimer, the term of this patent is extended or adjusted under 35 U.S.C. 154(b) by 603 days.

(21) Appl. No.: 12/326,056

(22) Filed: Dec. 1, 2008

(65) Prior Publication Data
US 2009/0165798 A1 Jul. 2, 2009

(30) Foreign Application Priority Data

Dec. 28, 2007 (CN) .......................... 2007 1 0306100

(51) Int. Cl.
*F16K 31/02* (2006.01)
*F16K 31/26* (2006.01)
*A61M 16/00* (2006.01)
*A62B 7/04* (2006.01)
*A62B 7/00* (2006.01)
*A62B 9/00* (2006.01)
*A62B 9/02* (2006.01)

(52) U.S. Cl. .......... 128/204.23; 128/204.18; 128/204.21; 128/204.22; 128/204.26; 128/205.23; 128/205.24

(58) Field of Classification Search ............. 128/203.12, 128/203.14, 204.18, 204.21–204.24, 204.26, 128/205.11, 205.23, 205.24, 920; *A61M 16/00; A62B 7/00, 7/04, 9/00, 9/02; F16K 31/02, F16K 31/26*
See application file for complete search history.

(56) References Cited

U.S. PATENT DOCUMENTS 3,961,627 A * 6/1976 Ernst et al. ............... 128/204.21
4,986,268 A * 1/1991 Tehrani ..................... 128/204.22
5,183,038 A * 2/1993 Hoffman et al. ......... 128/204.21
(Continued)

OTHER PUBLICATIONS

Wikipedia entry for "Mechanical Ventilation", http://en.wikipedia.org/wiki/Mechanical_ventilation, see highlighted portion, Sep. 6, 2011.*

*Primary Examiner* — Loan Thanh
*Assistant Examiner* — Oren Ginsberg
(74) *Attorney, Agent, or Firm* — Christopher L. Parmelee; Walker & Jocke

(57) ABSTRACT

The present invention discloses a method for improving control and detection precision of tidal volume by introducing R value, comprising the steps of: a plateau pressure Pplate is used to calculate a system compliance C with C=$\Delta$V/(Pplate–PEEP); $V_T$, the tidal volume obtained currently at patient terminal, is calculated with $V_T=\Delta V\times(C-Ctube)/C$, wherein $\Delta V$ is the variation of tidal volume, PEEP is the positive end expiratory pressure and Ctube is the compliance C of the line. Depending on the calculated $V_T$, the tidal volume which is actually obtained by the patients during this period, the processing unit calculates the tidal volume $V_T'$, which the airway is intended to reach during the next expiration period, by $V_T'=V_T+\Delta V_T\times K$ wherein K is a scaling factor for control and adjustment, $V_T$ is the tidal volume obtained by the patient during the current period, $V_T$set is the presetted tidal volume, $\Delta V_T=V_T$set$-V_T$. And the processing unit accordingly controls the opening position of the inspiratory valve during the next inspiration period, so as to achieve the purpose of improving control and detection of precision tidal volume.

4 Claims, 2 Drawing Sheets

U.S. PATENT DOCUMENTS

| | | | |
|---|---|---|---|
| 5,315,989 A * | 5/1994 | Tobia | 128/204.28 |
| 5,331,995 A * | 7/1994 | Westfall et al. | 137/8 |
| 5,494,028 A * | 2/1996 | DeVries et al. | 128/205.24 |
| 6,148,814 A * | 11/2000 | Clemmer et al. | 128/200.24 |
| 6,390,091 B1 * | 5/2002 | Banner et al. | 128/204.21 |
| 6,571,796 B2 * | 6/2003 | Banner et al. | 128/204.26 |

\* cited by examiner

METHOD FOR IMPROVING CONTROL AND DETECTION PRECISION OF TIDAL VOLUME BY A CALCULATION INTRODUCED WITH R VALUE

TECHNICAL FIELD

The present invention provides a novel method for improving control and detection precision of tidal volume. Meanwhile, during the calculation of tidal volume, the precision is improved with R value introduced, which can be applied to detection and diagnosis devices used in medical diagnosis, in particular, to the calculation and monitoring of tidal volume within an anesthesia machine or ventilator.

BACKGROUND

At present, for an anesthesia machine or a ventilator, there exists two methods for detecting tidal volume:

A sensor is placed at the patient terminal for real-time detecting data, which brings about the advantages that the monitored data is accurate, data process is not necessary, and the patient's status can be reflected in real-time. However, this method causes the disadvantage that the circuit from the machine to the patient's mouth is relatively long, resulting in possible interference during an operation by a surgeon. Furthermore, the relatively long circuit may affect the precision of the signals.

A sensor is embedded into the breathing circuit for real-time detecting data, which brings about the advantages that the problem of interference is eliminated and the signal is stable while there is disadvantage that the monitored data is not the real data of the patient, thus requiring a calculation to process it.

Generally, the compliance C is used for the compensation calculation of tidal volume.

The system compliance $C=\Delta V/(Pplate-PEEP)$.

wherein $\Delta V$ is the tidal volume variation, Pplate is the plateau pressure, and PEEP is the positive end expiratory pressure. $\Delta V$, Pplate and PEEP can be obtained through the monitoring of the sensor.

$$VT=\Delta V \times (C-Ctube)/C$$

wherein VT is the calculated tidal volume of the patient, Ctube is the compliance of the circuit and which is obtained by self-checking when the machine starts up.

The disadvantage of such calculation is that the calculated tidal volume VT of patient is not accurate.

SUMMARY OF THE INVENTION

In view of the inaccuracy of the calculation of patient's tidal volume VT mentioned above, the present invention provides a novel method for calculating tidal volume which is able to be used in medical devices including anesthesia machines and ventilators capable of affecting the respiratory system of patient, so as to improve the control and detection precision of tidal volume, therefore assuring the accuracy and safety of device during ventilation.

For solving the above problem, the basic idea of the present invention lies in that Pplate is used to calculate the value of system compliance C, wherein the plateau pressure Pplate can be measured by using the sensor generally used. A resistance R is introduced to calculate the plateau pressure Pplate for a more accurate value thereof, such that the improved control and detection precision of tidal volume is achieved.

The method for improving the detection precision of tidal volume according to the present invention comprises steps of:

a: A resistance value R is introduced to calculate the plateau pressure Pplate, wherein $Pplate=Ppeak-R\times L$, wherein L is peak flow rate, the peak pressure Ppeak and peak flow rate L are monitored by the sensor, and the resistance R is obtained by monitoring and calculation. Particularly, the resistance R is the patient's resistance and $R=\Delta P/L=(Ppeak-Pplate)/L$;

b: the plateau pressure Pplate is used to calculate the system compliance C with $C=\Delta V/(Pplate-PEEP)$, wherein $\Delta V$ is the variation of tidal volume, PEEP is the positive end expiratory pressure. $\Delta V$ and PEEP can be obtained through the monitoring of the sensor.

c: the patient's tidal volume VT obtained currently is calculated by $VT=\Delta V \times (C-Ctube)/C$, wherein Ctube is the compliance C of the line, which is obtained by self-checking when the machine starts up.

The value of the patient's tidal volume VT can be accurately calculated by the above calculation method.

With the method according to the present invention, the resistance R is introduced into the calculation of tidal volume to calculate the plateau pressure Pplate, which is in turn used to calculate the tidal volume, such that the accurate tidal volume VT of the patient can be obtained.

The method for improving tidal volume control precision according to the present invention is used in the medical devices for affecting breathing system of patient, comprising following steps:

A processing unit (1), which is valve-driven, drives the circuit system to alternatively enter the expiration period and the inspiration period so as to operate the system, and controls the opening position of a inspiratory valve (3) during the inspiration period;

At the end phase of expiration period, depending on the airway pressure value transmitted in real-time by an airway pressure sensor within one respiratory period, the processing unit calculates peak pressure and PEEP value, and at the same time calculates the value of $\Delta V$ depending on the flow rate value transmitted in real-time by flow rate sensors; and according to the above method, the processing unit calculates the tidal volume VT actually obtained at the patient terminal for current respiratory period, and calculates the tidal volume VT' which the airway is intended to reach for next expiration period by $VT'=VT+\Delta VT\times K$, wherein K is a scaling factor for control and adjustment, VT is the tidal volume obtained by the patient during the current period, VTset is the presetted tidal volume, $\Delta VT=VTset-VT$. The processing unit controls the opening position of the inspiratory valve during the next inspiration period.

It should be noted that both the above description and the following description are illustrative and intended to further describe the claimed present invention.

Besides the objects, features and advantages described above, the present invention has other objects, features and advantages. In conjunction with accompanying figures, the other objects, features and effects of the present invention will be described in more detail.

BRIEF DESCRIPTION OF THE DRAWINGS

The accompanying figures, included for constituting a part of the present specification and used for further understanding of the present invention, illustrate prefer embodiments and explain the principle of the present invention along with the description, in which.

DETAILED DESCRIPTION OF THE PREFERRED EMBODIMENTS

Figure 1:
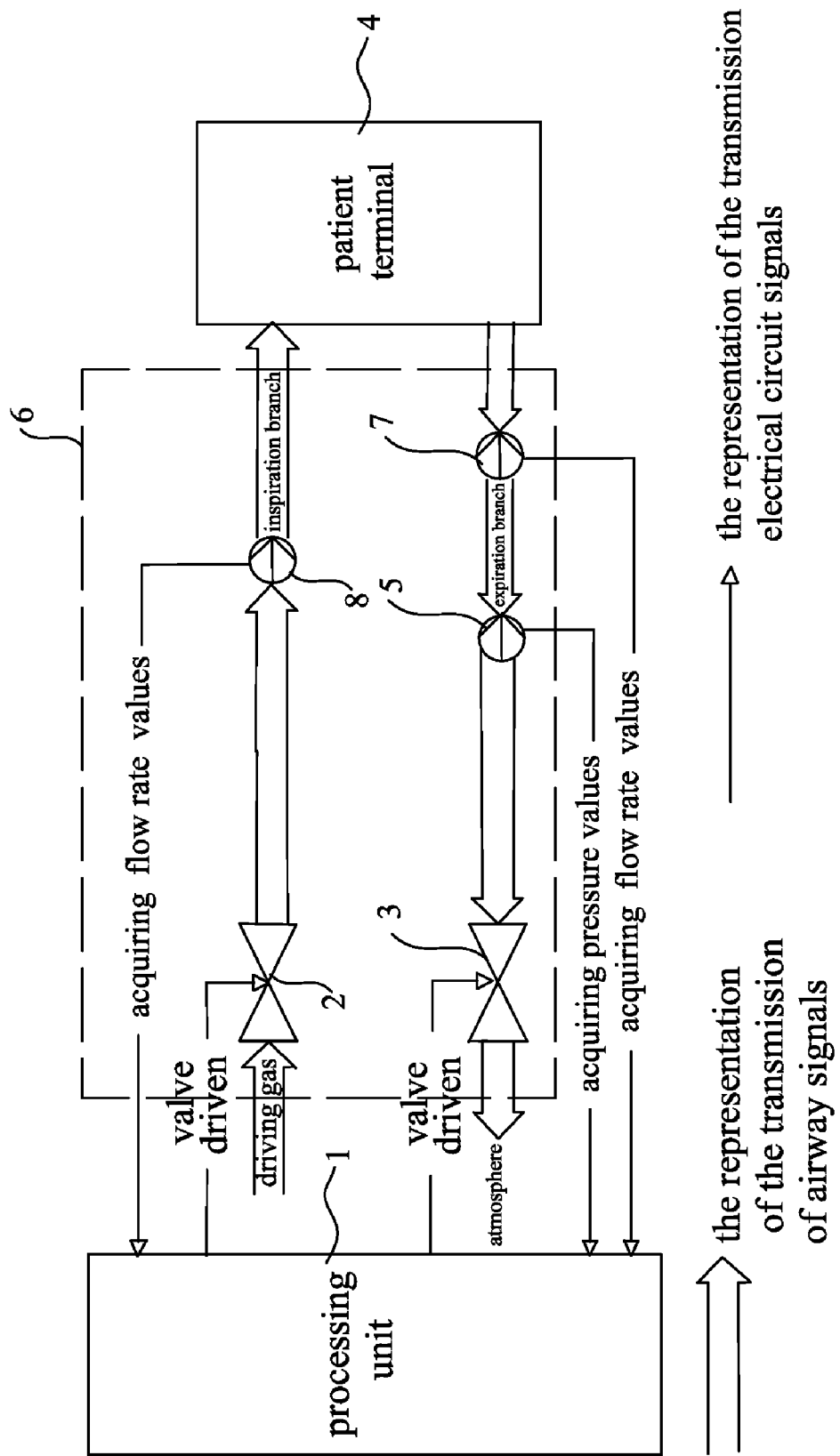
FIG. 1 is a view of the working principle of the method according to the present invention.

Hereinafter, the present invention is further set forth in conjunction with the best embodiment shown in the accompanying figures.

The device used for implementing the method according to the present invention comprises a processing unit 1, a airway system and a data acquiring and receiving unit. The airway system includes a respiratory circuit 6 and a driver line and a respiratory line at patient terminal 4 which are respectively connected to the outside of the respiratory circuit and the air bag. The respiratory line at patient terminal includes inspiration branch and expiration branch. A inspiratory valve 2 and a PEEP valve 3 which is used for discharging the driving gas to the atmosphere are connected in the driver. The sensor data acquiring and receiving unit for acquiring the airway peak pressure and PEEP value includes an airway pressure sensor 5 positioned in the airway, by which the airway peak pressure and PEEP value are acquired and transmitted to the processing unit 1. The processing unit 1 calculates the tidal volume at the patient terminal according to the related data obtained.

The working principle and process of the method are: during the inspiration period, the PEEP valve 3 is controlled to be closed and the inspiratory valve 2 is opened to be with presetted flow rate under the control of the process unit 1, the driving gas enters the outer chamber of the bellows positioned in the respiratory circuit 6 via the inspiratory valve 2, the air bag in the bellows is compressed to move downwards such that the gas within the air bag flows to the patient terminal 4 via the inspiration branch, enabling the patient to inhale the gas. Upon the processing unit 1 determines that the inspiration period is finished and the expiration period starts, the processing unit 1 controls the PEEP valve 3 to reach a certain opening position, and at this point the inspiratory valve is controlled to be closed and the gas returns inside the collapsed air bag of the bellows in the respiratory circuit 6 through the expiration branch from the patient terminal, pushing the air bag rising so as to exhaust the driving gas outside the bellows into the atmosphere through the PEEP valve 3 from the ventilator. Thus, the inspiration period is finished. During the inspiration period, the airway pressure sensor 5 transmits the airway pressure acquired during one respiratory period to the processing unit 1 in real-time. The process unit 1 calculates the peak pressure and PEEP value, and at the same time the flow rate sensors 7 and 8 transmit the values of flow rate to the processing unit 1 in real-time as well. The processing unit 1 calculates the value of $\Delta V$. According to the novel calculation method of the present invention, based on the obtained data, the processing unit 1 calculates the tidal volume VT, which is the tidal volume actually obtained at the patient terminal during this respiratory period, $VT'=VT+\Delta VT\times K$, wherein K is a scaling factor for control and adjustment, VT is the tidal volume obtained by the patient during the current period, VTset is the presetted tidal volume, $\Delta VT=VTset-VT$. VT', the tidal volume value which is expected to be reached by the airway during the next expiration period, is calculated. The processing unit 1 accordingly controls the opening position of the inspiratory valve 3 during the next period. Under the control of the processing unit 1, the system is circulated depending on the above steps until the tidal volume obtained at the patient terminal reaches the required control precision.

Figure 2:
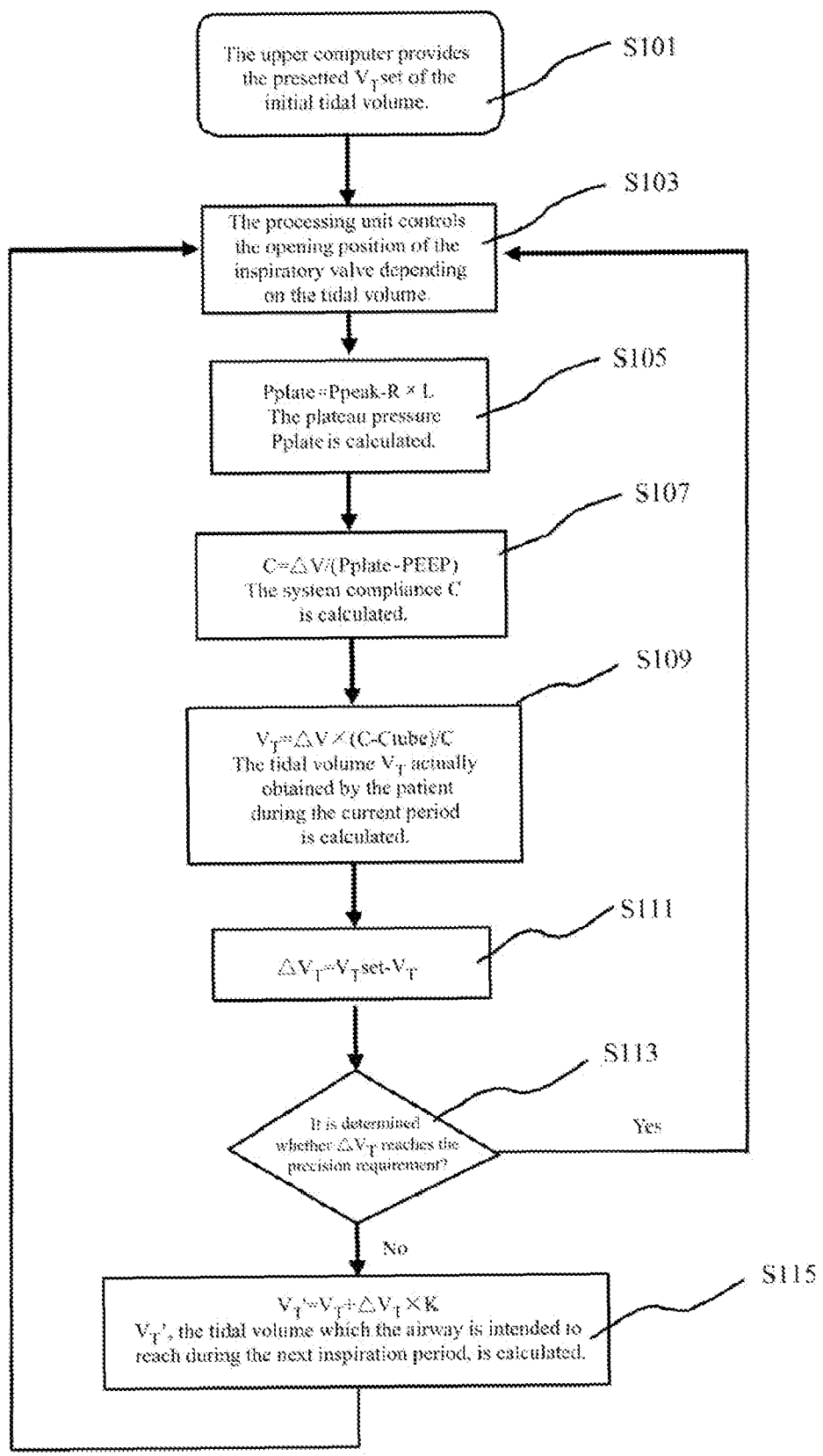
FIG. 2 is a flowchart of the method according to the present invention.

Based on the principle of the working process mentioned above, this method includes the steps as shown in FIG. 2.

Step S101: the upper computer provides the presetted value VTset of initial tidal volume and the initial operation is performed with such VTset as the reference.

Step S103: the processing unit controls the opening position of the inspiratory valve according to the tidal volume. In particular, the processing unit 1, via valve-driven, drives the airway system to alternatively enter the inspiration period and the expiration period so as to make the system operate, and controls the opening position of the inspiratory valve 3 during the inspiration period.

Step S105: the plateau pressure Pplate is calculated by Pplate=Ppeak−R×L, wherein the resistance R=$\Delta P/L$= (Ppeak−Pplate)/L, the peak pressure Ppeak and the peak flow rate L are obtained by the monitoring of the sensor;

Step S107: the system compliance C is calculated by C=$\Delta V$/(Pplate−PEEP) wherein $\Delta V$ is the tidal volume variation and PEEP is the positive end expiratory pressure. $\Delta V$ and PEEP can be obtained through the monitoring of the sensor. In particular, during the end phase of the expiration period, based on the airway pressure transmitted in real-time by the airway pressure sensor 5 during one inspiration period, the processing unit 1 calculates the peak pressure and PEEP value, and at the same time calculates the value of $\Delta V$ based on the flow rate value transmitted in real-time by the flow rate sensors 7 and 8.

Step S109: VT, the tidal volume, which is actually obtained by the patients during this period, is calculated by VT=$\Delta V\times$(C−Ctube)/C, wherein Ctube is the compliance of the line, which is obtained by self-checking when the machine starts up.

Step S111: $\Delta VT$, the deviation of the tidal volume, is calculated by $\Delta VT=VTset-VT$, wherein VTset is the presetted tidal volume, and VT is the tidal volume actually obtained by the patient during the period.

Step S113: it is determined whether VT reaches the requirement of the precision. If yes, returns to S103, and still operates according to the tidal volume of the last time; If No, performs the Step S115.

Step S115: the tidal volume VT', which the airway is intended to reach for next expiration period, is calculated by $VT'=VT+\Delta VT\times K$, wherein K is a scaling factor for control and adjustment, VT is the tidal volume obtained by the patient during the current period, $\Delta VT=VTset-VT$. And then returns to Step S103. The processing unit 1 accordingly controls the opening position of the inspiratory valve 3 during the next inspiration period.

The method according to the present invention is experimentally verified in the anesthesia machine or ventilator. It is proven that the solution of method is feasible, the measurement is accurate, and it is real-time, safe and reliable.

The above description is merely the preferred embodiment of the present invention and is not used to limit the present invention. As for those skilled in the art, various variations, changes and omission can be made to the present invention. All modifications, substitutions, improvements and so on, within the spirit and principle of the present invention, should be contained in the scope of the present invention.

REFERENCE NUMBERS EXPLANATION 1 processing unit
2 inspiratory valve
3 PEEP valve
4 patient terminal
5 airway pressure sensor
6 respiratory circuit
7 flow rate sensor 8 flow rate sensor

What is claimed is:

1. A method for improving tidal volume detection precision which is used in medical devices for affecting the breathing system of patient, characterized in that it includes the following steps:
   a) a processing unit (1), through the driving of a valve, drives an airway system to alternatively enter an inspiration period and an expiration period so as to operate the airway system, and controls an opening position of an inspiratory valve (3) during the inspiration period;
   b) at an end phase of the expiration period, depending on the airway pressure transmitted in real-time by an airway pressure sensor within a respiratory period, the processing unit (1) calculates peak pressure and PEEP value, and at the same time calculates the value of $\Delta V$, the variation of tidal volume, depending on the flow rate values transmitted in real-time by flow rate sensors (7 and 8); and
   c) the processing unit (1) calculates the tidal volume $V_T$ actually obtained at the patient terminal during a current respiratory period, using the formula $V_T = \Delta V \times (C - Ctube)/C$, wherein C is system compliance, Ctube is the compliance C of a line, and calculates the tidal volume $V_T'$ which the airway is intended to reach for the next expiration period, using the formula $V_T' = \Delta V_T + \Delta V_T \times K$, wherein K is a scaling factor for control and adjustment, $\Delta V_T = V_T set - V_T$, $V_T set$ is the presetted tidal volume, and the processing unit accordingly controls the opening position of the inspiratory valve (3) during a next inspiration period.

2. A method for improving tidal volume detection precision according to claim 1, characterized in that, the medical device includes an anesthesia machine or a ventilator.

3. A method for improving tidal volume detection precision which is used in medical devices for affecting the breathing system of patient, characterized in that it includes the following steps:
   Step S101: an upper computer provides the presetted value $V_T set$ of an initial tidal volume;
   Step S103: a processing unit controls an opening position of an inspiratory valve according to the initial tidal volume;
   Step S105: a plateau pressure Pplate is calculated by Pplate=Ppeak−R×L, wherein the resistance R=$\Delta P/L$=(Ppeak−Pplate)/L, the peak pressure Ppeak and the peak flow rate L are obtained by the monitoring of a sensor;
   Step S107: a system compliance C is calculated by C=$\Delta V$/(Pplate−PEEP) wherein $\Delta V$ is the tidal volume variation and PEEP is the positive end expiratory pressure, $\Delta V$ and PEEP can be obtained through the monitoring of a sensor;
   Step S109: $V_T$, the tidal volume which is actually obtained by the patients during a current period, is calculated by $V_T = \Delta V \times (C - Ctube)/C$ wherein Ctube is the compliance of a line, which is obtained by self-checking when the medical device starts up;
   Step S111: $\Delta V_T$, the deviation of the tidal volume, is calculated by $\Delta V_T = V_T set - V_T$, wherein $V_T set$ is the presetted tidal volume, and $V_T$ is the tidal volume actually obtained by the patient during this period;
   Step S113: it is determined whether $V_T$ reaches requirement of precision, wherein if yes, returns to S103, and still operates depending on the tidal volume of the last time, while if no, performs Step S115; and
   Step S115: the tidal volume $V_T'$, which the airway is intended to reach for a next expiration period, is calculated by $V_T' = V_T + \Delta V_T \times K$, wherein K is a scaling factor for control and adjustment, $V_T$ is the tidal volume actually obtained by the patient during the current period, $\Delta V_T = V_T set - V_T$, and returns to Step S103 and the processing unit (1) accordingly controls the opening position of the inspiratory valve (3) during a next inspiration period.

4. A method for improving tidal volume detection precision according to claim 3, characterized in that, the medical device include an anesthesia machine or an ventilator.

\* \* \* \* \*

UNITED STATES PATENT AND TRADEMARK OFFICE
CERTIFICATE OF CORRECTION

PATENT NO.         : 8,066,003 B2
APPLICATION NO.    : 12/326056
DATED              : November 29, 2011
INVENTOR(S)        : Yumeng Cong, Fei Cheng and Wei Wang It is certified that error appears in the above-identified patent and that said Letters Patent is hereby corrected as shown below:

Title Page, Item (75) Inventors replace:
"Fei Chang" with --Fei Cheng--.

Signed and Sealed this
Twenty-first Day of February, 2012

David J. Kappos
*Director of the United States Patent and Trademark Office*